US011534596B2

(12) United States Patent
Schafir et al.

(10) Patent No.: US 11,534,596 B2
(45) Date of Patent: Dec. 27, 2022

(54) PULSATILE BLOOD PUMP VIA CONTRACTION WITH SMART MATERIAL

(71) Applicant: HeartWare, Inc., Miami Lakes, FL (US)

(72) Inventors: David A. Schafir, Miami Shores, FL (US); Fernando Casas, Miami Lakes, FL (US)

(73) Assignee: Heartware, Inc., Miami Lakes, FL (US)

(*) Notice: Subject to any disclaimer, the term of this patent is extended or adjusted under 35 U.S.C. 154(b) by 109 days.

(21) Appl. No.: 17/100,319

(22) Filed: Nov. 20, 2020

(65) Prior Publication Data
US 2021/0213185 A1    Jul. 15, 2021

Related U.S. Application Data

(60) Provisional application No. 62/958,778, filed on Jan. 9, 2020.

(51) Int. Cl.
| A61M 60/88 | (2021.01) |
| A61M 60/178 | (2021.01) |
| A61M 60/81 | (2021.01) |
| A61M 60/857 | (2021.01) |
| A61M 60/148 | (2021.01) |
| A61M 60/232 | (2021.01) |

(52) U.S. Cl.
CPC ........ *A61M 60/857* (2021.01); *A61M 60/148* (2021.01); *A61M 60/232* (2021.01); *A61M 2205/0294* (2013.01); *A61M 2205/04* (2013.01)

(58) Field of Classification Search
CPC .............. A61M 60/857; A61M 60/148; A61M 60/205; A61M 60/122; A61M 2205/04; A61M 60/232; A61M 2205/3331; A61M 2205/3337; A61M 2205/3351; A61M 2205/3355; A61M 60/00; A61M 60/135; A61B 5/026; A61B 5/02158
See application file for complete search history.

(56) References Cited

U.S. PATENT DOCUMENTS

| 5,092,878 A | 3/1992 | Miyata |
| 6,293,901 B1 | 9/2001 | Prem |
| 6,688,861 B2 | 2/2004 | Wampler |
| 7,575,423 B2 | 8/2009 | Wampler |
| 7,976,271 B2 | 7/2011 | LaRose et al. |
| 8,007,254 B2 | 8/2011 | Larose et al. |
| 8,419,609 B2 | 4/2013 | Shambaugh, Jr. et al. |

(Continued)

FOREIGN PATENT DOCUMENTS

| CA | 2165164 A1 | 10/1995 |
| WO | WO-2005006975 A1 * | 1/2005 ......... A61B 5/02158 |

OTHER PUBLICATIONS

Scudellari, "A Fitbit for the Stomach > The ingestible, self-powered device tracks food ingestion," IEEE Spectrum, Oct. 11, 2017, 5 pp.

(Continued)

*Primary Examiner* — Jon Eric C Morales
(74) *Attorney, Agent, or Firm* — Shumaker & Sieffert, P.A.

(57) ABSTRACT

An inflow cannula for an implantable blood pump, the inflow cannula defining an inlet at a proximal end, an opposite distal end, and a lumen therebetween, the inflow cannula being configured to constrict the lumen.

20 Claims, 3 Drawing Sheets

(56) References Cited

U.S. PATENT DOCUMENTS

| | | |
|---|---|---|
| 8,506,471 B2 | 8/2013 | Bourque |
| 8,512,013 B2 | 8/2013 | LaRose et al. |
| 9,217,442 B2 | 12/2015 | Wiessler et al. |
| 9,561,313 B2 | 2/2017 | Taskin |
| 9,907,891 B2 | 3/2018 | Wiessler et al. |
| 2009/0112312 A1 | 4/2009 | LaRose et al. |
| 2012/0149970 A1 | 6/2012 | Jeevanandam et al. |
| 2012/0245681 A1 | 9/2012 | Casas et al. |
| 2013/0066139 A1 | 3/2013 | Wiessler et al. |
| 2013/0289335 A1 | 10/2013 | Thompson et al. |
| 2013/0303832 A1 | 11/2013 | Wampler |
| 2014/0288354 A1 | 9/2014 | Timms et al. |
| 2015/0322940 A1 | 11/2015 | Horvath et al. |
| 2016/0045654 A1 | 2/2016 | Connor |
| 2016/0271309 A1 | 9/2016 | Throckmorton et al. |
| 2017/0173240 A1 | 6/2017 | Taskin et al. |
| 2017/0281842 A1 | 10/2017 | LaRose et al. |
| 2018/0200421 A1 | 7/2018 | Wiessler et al. |
| 2018/0303989 A1 | 10/2018 | Casas |
| 2018/0335037 A1 | 11/2018 | Shambaugh et al. |
| 2021/0113751 A1 | 4/2021 | Casas et al. |

OTHER PUBLICATIONS

Sarah Fields, It's A Bird, It's A Plane: Flow Patterns Around An Oscillating Piezoelectric Fan Blade, Oct. 2017, Comsol Multiphysics, 3 pages.

International Search Report and Written Opinion dated Dec. 9, 2020 for corresponding International Application No. PCT/US2020/051386; International Filing Date: Sep. 18, 2020 consisting of 9 pages.

International Search Report and Written Opinion dated Apr. 13, 2021, for corresponding International Application No. PCT/US2020/063569; International Filing Date: Dec. 7, 2020 consisting of 8-pages.

* cited by examiner

PULSATILE BLOOD PUMP VIA CONTRACTION WITH SMART MATERIAL

CROSS-REFERENCE TO RELATED APPLICATION

This application is related to and claims priority to U.S. Provisional Patent Application Ser. No. 62/958,778, filed Jan. 9, 2020, the entirety of which is incorporated herein by reference.

FIELD

The present technology is generally related to implantable blood pumps, and in particular, an inflow cannula for an implantable blood pump.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

If an implantable blood pump fails, as the heart continues to pump blood, blood may flow into the blood pump where it will reside owing to a lack of pressure to move the blood into the aorta. In such a situation, blood flows into the pump rather than into the aorta. Moreover, owing to pressure into the aorta, blood blows into the pump from a graft connecting the pump to the aorta, rather than circulate around the body. When such a situation occurs, a patient's life is at risk.

SUMMARY

The techniques of this disclosure generally relate to an inflow cannula for an implantable blood pump.

In one aspect, the present disclosure provides an inflow cannula for an implantable blood pump, the inflow cannula defining an inlet at a proximal end, an opposite distal end, and a lumen therebetween, the inflow cannula being configured to constrict the lumen.

In another aspect of this embodiment, the inflow cannula includes an inner tube and an outer tube, and wherein the inner tube defines the lumen, and wherein the inner tube includes a flexible material.

In another aspect of this embodiment, the flexible material flexes to constrict the lumen.

In another aspect of this embodiment, flexion of the flexible material does not constrict the inlet.

In another aspect of this embodiment, the inner tube includes a piezoelectric element.

In another aspect of this embodiment, the piezoelectric element is coupled to a power source.

In another aspect of this embodiment, the inner tube defines an inner diameter and an outer diameter, and wherein the piezoelectric element is disposed between the inner diameter and the outer diameter.

In another aspect of this embodiment, the implantable blood pump is a centrifugal flow blood pump.

In another aspect of this embodiment, the inner tube defines a substantially hyperboloid shape when the inflow cannula is constricted.

In another aspect of this embodiment, the inflow cannula is configured to occlude the lumen.

In one embodiment, a method of preventing regurgitant flow in an implantable blood pump having an inflow cannula defining a lumen therethrough, the implantable blood pump being coupled to a power source configured to provide power to the implantable blood pump includes substantially occluding the lumen of the inflow cannula if a complete loss of power to the implantable blood pump is detected.

In another aspect of this embodiment, the inflow cannula includes an inner tube and an outer tube, and wherein the inner tube defines the lumen, and wherein the inner tube includes a flexible material.

In another aspect of this embodiment, the inner tube includes a piezoelectric element.

In another aspect of this embodiment, the piezoelectric element is coupled to the power source.

In another aspect of this embodiment, the inner tube defines an inner diameter and an outer diameter, and wherein the piezoelectric element is disposed between the inner diameter and the outer diameter.

In another aspect of this embodiment, the inner tube flexes to constrict the lumen of the inflow cannula when the complete loss of power is detected.

In another aspect of this embodiment, the inner tube defines a substantially hyperboloid shape when the inflow cannula is constricted.

In another aspect of this embodiment, if power is restored the implantable blood pump, the inner tube flexed to define a substantially planar shape.

In another aspect of this embodiment, the implantable blood pump is a centrifugal flow blood pump.

In one embodiment, an inflow cannula for an implantable blood pump defines an inlet at a proximal end, an opposite distal end, and a lumen therebetween, the inflow cannula includes an outer tube and a concentric inner tube, the inner tube being flexible independently of the outer tube and including a piezoelectric element embedded therein, the piezoelectric element being configured to flex to constrict the lumen when an electric potential is applied to the piezoelectric element, the inner tube defining a substantially hyperboloid shape to constrict the lumen.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
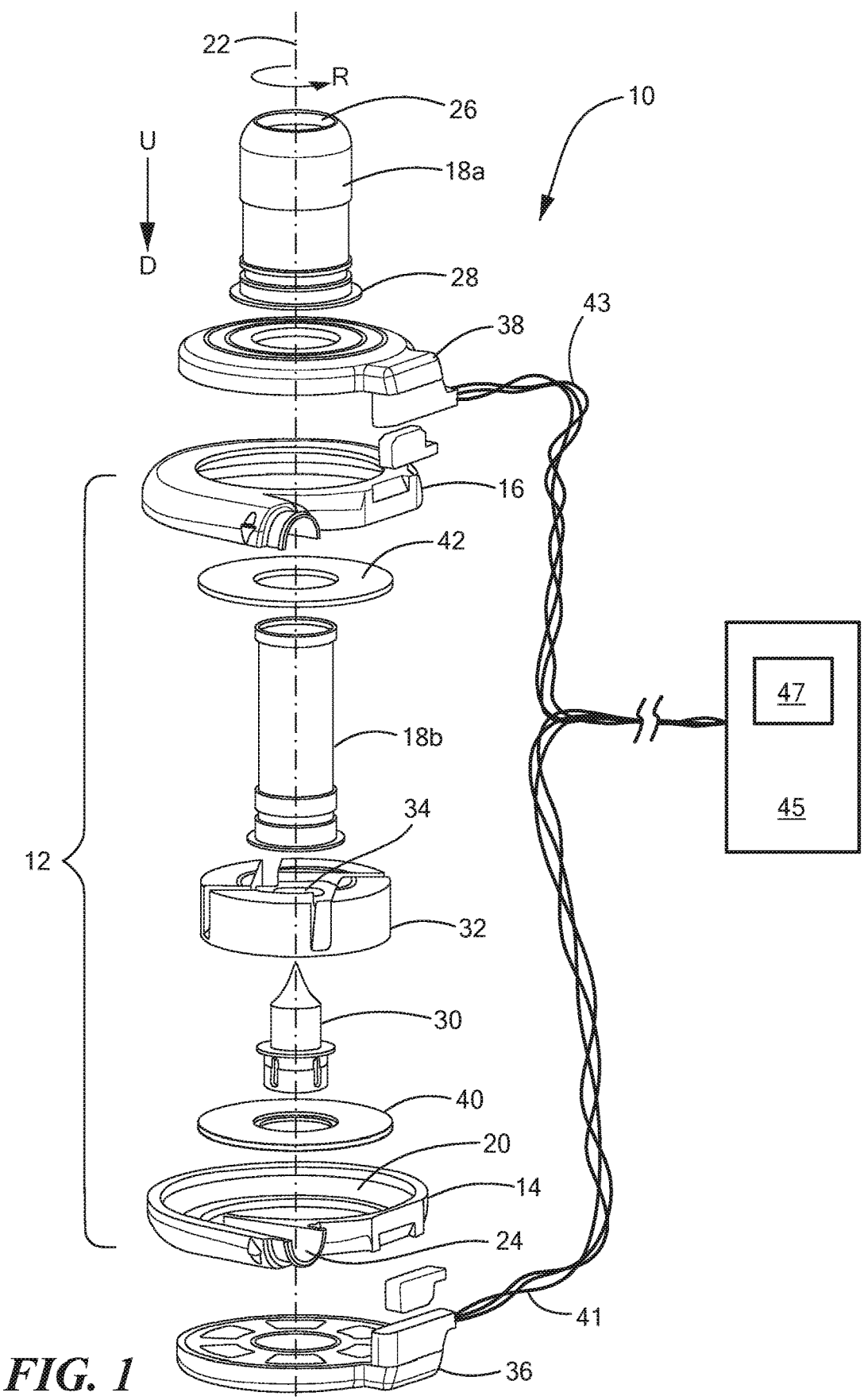
FIG. 1 is a disassembled view of an implantable blood pump constructed in accordance with the principles of the present application.

Referring now to the drawings in which like reference designators refer to like elements there is shown in FIG. 1 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

Figure 2:
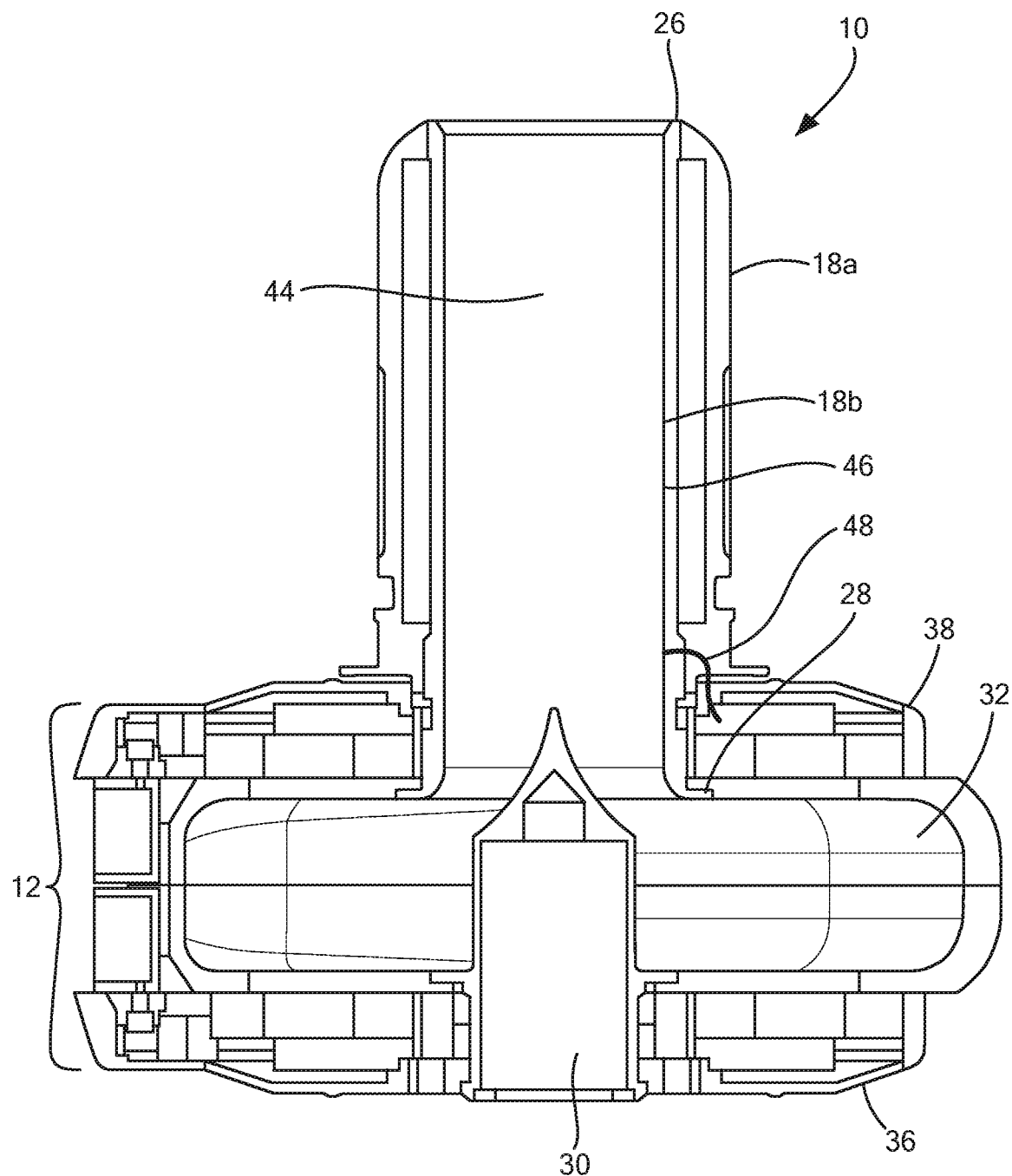
FIG. 2 is a cross-sectional view of the pump shown in FIG. 1.

Referring now to FIGS. 1 and 2, the inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc-shaped ferromagnetic rotor 32 with a central hole 34 is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 (FIG. 1) are provided on the first stator 36 and the second stator 38 respectively for connecting the coils to a source of power such as a controller 45 having processing circuitry 47. The controller is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation. For example, the bearings maintain the rotor 32 out of contact from respective non-ferromagnetic discs 40 and 42. The general arrangement of the components described above may be similar to the blood pump 10 used in the MCSD sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 3:
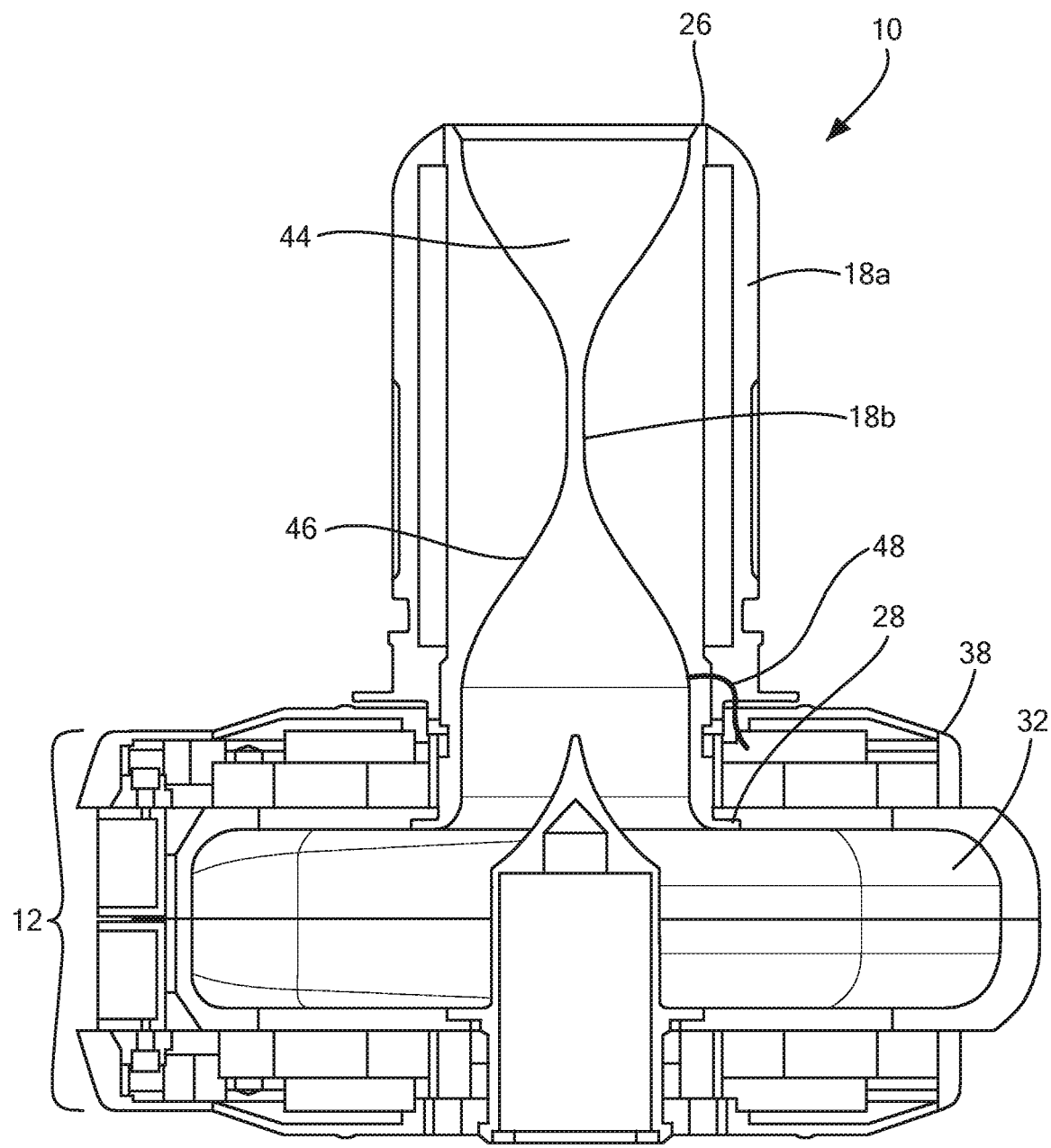
FIG. 3 is another cross-sectional view of the pump shown in FIG. 1 with the inlet constricted.

Referring now to FIG. 3, the inner tube 18b may be configured to be deformed or otherwise flex to constrict a lumen 44 of the inflow cannula 18. That is, the inflow cannula 18 may be configured to completely or partially constrict the flow path extending from the proximal end 26 to the distal end 28 of the inflow cannula 18. In one configuration, the inner tube 18b may define a substantially hyperboloid shape or hour-glass shape when flexed which does not constrict the inlet of the inflow cannula. In other configurations, the inner tube 18 may flex or otherwise deform to define any shape to constrict or occlude completely the lumen 44 of the inflow cannula 18. In one configuration, the inner tube 18b flexes by pneumatic pressure to collapse the cannula. In such a configuration, the inner tube 18b may be a flexible polymer or other flexible material and the pneumatic components may be disposed between the inner tube 18b and the outer tube 18a as to isolate them from the blood flow.

In another configuration, the inner tube 18b may include a piezoelectric element 46 embedded or otherwise disposed within the inner tube 18b and isolated from the blood flow. The piezoelectric element 46 may be coupled to the same power source as the blood pump 10 such that an electric potential may be applied to the piezoelectric element 46 to deform it. For example, a conductor 48 such as a wire may extend into the space between the inner tube 18 and the outer tube 18b. The conductor 48 may connect with the conductors that provide power to the pump 10. In other configurations, an electronics module (not shown) is disposed between the inner tube 18b and the outer tube 18a, the electronics module having its own integrated power source to apply an electric potential to the inner tube 18b. In one configuration, the inner tube 18b may constrict the inflow cannula 18 such that it remains in a constricted configuration during operation of the pump. For example, if the pump is a right ventricular assist device, less flow may be needed and thus the change in flow may be achieved by constricting the inflow cannula 18 without changing any other properties of the pump.

Optionally, in cases where the pump stops, for example, loss of power or a short circuit, regurgitant flow may occur, where blood flows into the pump and not into the aorta. To prevent such an occurrence, the inner tube 18 may be biased in a substantially open configuration, as shown in FIG. 2. In other words, if the pump is operational an electric potential may be applied to the piezoelectric element 46 which causes the inner tube to flex to a substantially planar configuration that keeps the lumen 44 open and unconstrained. When power is lost and the electric potential is no longer applied to the inner tube 18b, the inner tube 18b relaxes to its unconstrained configuration constricting the lumen 44. In this manner, in power is lost, blood is prevented from flowing into and out of the pump.

In another configuration, the controller may be configured to selectively apply an electric potential to the piezoelectric element 46 to cause the inner tube 18b to deform at predetermined intervals to cause pulsatility. For example, the controller may be configured to apply the electric potential to the inner tube 18b in synchrony or asynchronously with the cardiac cycle to provide pulsatile flow.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A blood pump system, comprising:
   an inflow cannula defining an inlet at a proximal end, an opposite distal end, and a lumen defining a flow path for a blood flow therebetween;
   a power source; and
   a piezoelectric element configured to cause the inflow cannula to flex to constrict the flow path when the power source applies an electric potential to the piezoelectric element.

2. The blood pump system of claim 1, wherein the inflow cannula includes an inner tube and an outer tube, and wherein the inner tube defines the lumen, and wherein the inner tube includes a flexible material.

3. The blood pump system of claim 2, wherein the flexible material is configured to flex to constrict the lumen.

4. The blood pump system of claim 3, wherein the flexible material is configured such that flexion of the flexible material does not constrict the inlet.

5. The blood pump system of claim 2, wherein the piezoelectric element is configured to cause the inner tube to flex to constrict the flow path.

6. The blood pump system of claim 2, wherein the inner tube defines an inner diameter and an outer diameter, and wherein the piezoelectric element is disposed between the inner diameter and the outer diameter.

7. The blood pump system of claim 1, further comprising an implantable blood pump fluidically coupled to the lumen, wherein the implantable blood pump is a centrifugal flow blood pump.

8. The blood pump system of claim 2, wherein the inner tube defines a substantially hyperboloid shape when the inflow cannula is constricted.

9. The blood pump system of claim 1, wherein the inflow cannula is configured to flex to substantially completely occlude the lumen.

10. The blood pump system of claim 1, further comprising an implantable blood pump configured to receive power to drive the blood flow through the lumen from the inlet to the opposite distal end, wherein the piezoelectric element is configured to cause the inflow cannula to substantially occlude the lumen when the implantable blood pump fails to receive the power.

11. The blood pump system of claim 1, further comprising processing circuitry configured to cause the power source to apply the electric potential to the piezoelectric element at a predetermined interval to cause a pulsatility in a blood flow though the lumen.

12. A method comprising:
    detecting, using processing circuitry, a loss of power to an implantable blood pump, the implantable blood pump being fluidically coupled to an inflow cannula and being configured to receive power from a power source; and
    substantially occluding, using the inflow cannula, a lumen of the inflow cannula when the processing circuitry detects the loss of power, wherein substantially occluding the lumen comprises causing, by a piezoelectric element, the inflow cannula to flex to constrict a flow path through the lumen.

13. The method of claim 12, wherein the inflow cannula includes an inner tube and an outer tube, wherein the inner tube defines the lumen, wherein causing the inflow cannula to flex comprises flexing the inner tube to substantially occlude the lumen.

14. The method of claim 12, wherein causing the piezoelectric element to cause the inflow cannula to flex comprises applying, using the power source, an electric potential to the piezoelectric element.

15. The method of claim 13, wherein the inner tube defines a substantially hyperboloid shape when the inflow cannula is flexed.

16. The method of claim 15, further comprising, restoring power to the implantable blood pump, wherein the inner tube defines a substantially planar shape to open the lumen when power is restored to the implantable blood pump.

17. The method of claim 12, further comprising pumping, using the implantable blood pump, blood through the flow path.

18. The method of claim 12, further comprising causing, using the processing circuitry, the piezoelectric element to cause the inflow cannula to flex at a predetermined interval to cause a pulsatility in the blood flow.

19. A blood pump system, comprising:
- an inflow cannula for an implantable blood pump, the inflow cannula defining an inlet at a proximal end, an opposite distal end, and a lumen therebetween, the inflow cannula including an outer tube and a concentric inner tube, the inner tube being flexible independently of the outer tube; and
- a piezoelectric element configured to cause the inner tube to flex to constrict the lumen when an electric potential is applied to the piezoelectric element, the inner tube defining a substantially hyperboloid shape to constrict the lumen.

20. The blood pump system of claim 19, further comprising an implantable blood pump configured to receive power to drive the blood flow through the lumen from the inlet to the opposite distal end, wherein the piezoelectric element is configured to cause the inflow cannula to substantially occlude the lumen when the implantable blood pump fails to receive the power.

* * * * *